US012616431B2

(12) United States Patent
Nakanishi et al.

(10) Patent No.: US 12,616,431 B2
(45) Date of Patent: May 5, 2026

(54) IMAGING CONTROL SYSTEM AND IMAGING CONTROL METHOD

(71) Applicants: KABUSHIKI KAISHA TOSHIBA, Toyko (JP); TOSHIBA ENERGY SYSTEMS & SOLUTIONS CORPORATION, Kawasaki (JP)

(72) Inventors: Kosuke Nakanishi, Tokyo (JP); Yasushi Iseki, Yokohama Kanagawa (JP)

(73) Assignees: KABUSHIKI KAISHA TOSHIBA, Tokyo (JP); TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 166 days.

(21) Appl. No.: 18/419,966

(22) Filed: Jan. 23, 2024

(65) Prior Publication Data

US 2024/0156424 A1      May 16, 2024

Related U.S. Application Data

(63) Continuation of application No. PCT/JP2021/038227, filed on Oct. 15, 2021.

(51) Int. Cl.
*A61B 6/00*          (2024.01)
*A61B 5/113*          (2006.01)
(52) U.S. Cl.
CPC ............ *A61B 6/4447* (2013.01); *A61B 5/113* (2013.01); *A61B 6/547* (2013.01)
(58) Field of Classification Search
None
See application file for complete search history.

(56) References Cited

U.S. PATENT DOCUMENTS

2010/0067739 A1      3/2010  Mostafavi et al.
2010/0104070 A1      4/2010  Knox et al.
(Continued)

FOREIGN PATENT DOCUMENTS

JP          2012-508035 A      4/2012
JP          2015-29793 A      2/2015
(Continued)

OTHER PUBLICATIONS

International Search Report with English Translation of International Patent Application No. PCT/JP2021/038227 dated Dec. 28, 2021 (4 pages).

*Primary Examiner* — Hoon K Song
(74) *Attorney, Agent, or Firm* — Foley & Lardner LLP

(57)          ABSTRACT

According to one embodiment, an imaging control system comprising: an X-ray imaging device; a respiratory monitor; and a control calculating device; the control calculating device comprising: a respiratory waveform divider to slice at least one of cycle and amplitude in a respiratory waveform of the respiratory motion included in the respiratory data into multiple specific fragments, an image data sorter to acquire a rotational angle indicating a rotational position of the rotating gantry from a gantry controller for controlling a rotation of the rotating gantry, and to sort the X-ray images contained in the image data every specific fragment into multiple X-ray images, and a three-dimensional reconstructor to reconstruct the multiple X-ray images categorized every specific fragment based on the rotational angle of the rotating gantry at shooting to generate multiple three-dimensional reconstructed images.

14 Claims, 12 Drawing Sheets

(56) References Cited

U.S. PATENT DOCUMENTS

| | | | |
|---|---|---|---|
| 2013/0259338 A1* | 10/2013 | Brehm | G06T 11/008 |
| | | | 382/131 |
| 2015/0036793 A1 | 2/2015 | Umekawa et al. | |
| 2016/0354047 A1* | 12/2016 | Huston | A61B 6/5288 |
| 2017/0209716 A1 | 7/2017 | Lugosi et al. | |
| 2021/0268312 A1 | 9/2021 | Miyamoto et al. | |
| 2022/0313180 A1* | 10/2022 | Baba | A61N 5/1049 |

FOREIGN PATENT DOCUMENTS

| | | |
|---|---|---|
| JP | 2015-517837 A | 6/2015 |
| JP | 2021-45459 A | 3/2021 |
| WO | WO-2008043378 A1 | 4/2008 |
| WO | WO-2020/012785 A1 | 1/2020 |
| WO | WO-2021/053891 A1 | 3/2021 |

* cited by examiner

IMAGING CONTROL SYSTEM AND IMAGING CONTROL METHOD

CROSS-REFERENCE TO RELATED APPLICATION

This application is a Continuation application of No. PCT/JP2021/038227, filed on Oct. 15, 2021, the entire contents of which are incorporated herein by reference.

TECHNICAL FIELD

Embodiments of the present invention relate to technology of controlling imaging.

BACKGROUND

Radiation therapy involves irradiating an affected area of a patient with radioactive rays to damage the cells in that area. If the irradiation is not accurately directed to the affected area in such a case, normal tissues may also be damaged. Accordingly, computed tomography (CT) is introduced in advance to determine the three-dimensional geometry of the affected area, so that a treatment regimen is formulated to most effectively irradiate the affected area other than normal tissue with radioactive rays. In order to irradiate the affected area with radioactive rays in accordance with this treatment regimen, the body posture of the patient at a time of treatment regimen must be aligned with the body posture of the patient at the time of treatment. The three-dimensional reconstructed image output from the CT imaging device is thus sectioned into a CT image at the time of treatment regimen, and this CT image is checked against an X-ray image taken from an X-ray imaging device in the treatment room immediately before treatment to determine a position of the affected area accurately. However, the X-ray imaging device can merely acquire a two-dimensional image of a patient; hence, it is difficult to perform highly accurate checking of the X-ray image against the reconstructed image obtained by the CT imaging device.

Some conventional techniques involve recognition of the three-dimensional position of the affected area captured during CT imaging, selection of an image that satisfies the conditions for irradiation with radioactive rays, performs reconstruction of the image to generate a CT image. This technique allows the affected area to be irradiated with radioactive rays as per the treatment regimen, even if breathing or other movements occur. Since this technique, however, selects only images that satisfy the conditions for irradiation, it does not accurately find changes in the location of the affected area. If the relative configuration of the skeletal and organs at the time of treatment regimen shift immediately prior to treatment, for example, it is difficult to distinguish whether such a shift is due to differences in the conditions of the patient on that day or to normal respiratory motion.

Another technique is also known that slices the amplitude of a respiratory waveform into multiple fragments and generates a tomographic image (CT image) using only projection images corresponding to a certain fragment. For example, use of only a projection image corresponding to a fragment of minimum amplitude can generate a tomogram corresponding to the state of maximum expiration. However, this technique is intended to reduce artifacts in tomographic images but not to find the condition of the patient over the entire respiratory motion that fluctuates between maximum inspiration and expiration.

PRIOR ART DOCUMENT

Patent Document

[Patent Document 1] JP 2015-29793 A
[Patent Document 2] JP 2010-505562 A
[Patent Document 3] JP 2021-45459 A

SUMMARY

Problem to be Solved by Invention

An object of the present invention is to provide a technique of controlling imaging that can accurately find the condition of the patient, which fluctuates with respiratory motion, in computed tomography for radiation therapy.

Means for Solving Problem

In one embodiment of the present invention, an imaging control system comprising: an X-ray imaging device to rotate together with a rotating gantry around a patient, to radiate X-rays to the patient for taking multiple two-dimensional X-ray images, and to output image data including the multiple two-dimensional X-ray images; a respiratory monitor to watch respiratory motion of the patient and to output respiratory data indicating the respiratory motion; and a control calculating device to acquire image data from the X-ray imaging device and to acquire the respiratory data from the respiratory monitor; the control calculating device comprising: a respiratory waveform divider to slice at least one of cycle and amplitude in a respiratory waveform of the respiratory motion included in the respiratory data into multiple specific fragments, an image data sorter to acquire a rotational angle indicating a rotational position of the rotating gantry from a gantry controller for controlling a rotation of the rotating gantry, and to sort the X-ray images contained in the image data every specific fragment into multiple X-ray images, and a three-dimensional reconstructor to reconstruct the multiple X-ray images categorized every specific fragment based on the rotational angle of the rotating gantry at shooting to generate multiple three-dimensional reconstructed images.

Effects of Invention

According to embodiments of the present invention, it is possible to provide a technique of controlling imaging that can accurately find the condition of the patient, which fluctuates with respiratory motion, in computed tomography for radiation therapy.

DETAILED DESCRIPTION (First embodiment) The following is a detailed description of embodiments of the imaging control system and the method of controlling imaging with reference to the drawings. A first embodiment will now be described with reference to FIGS. 1 through 7.

Figure 1:
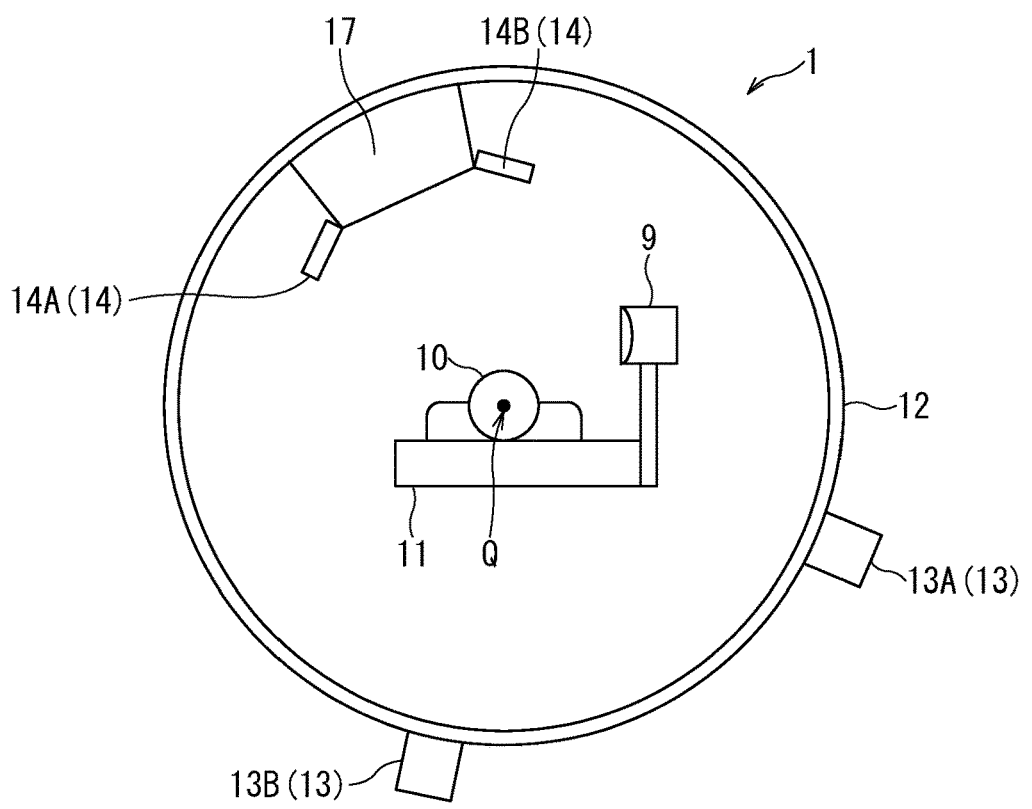
FIG. 1 is a cross-sectional view of a rotating gantry used in an imaging control system of a first embodiment.

Reference numeral 1 in FIG. 1 indicates an imaging control system (CT imaging system for radiation therapy) of the first embodiment. This imaging control system 1 irradiate an affected areas and organs of a patient 10 with X-rays (radioactive rays for imaging) to take image data of the affected areas of the patient 10 and generates three-dimensional reconstructed images using the resulting image data. This reconstructed image is a computed tomographic (CT) image of the patient 10.

The imaging control system 1 is applied to a particle beam therapy device (not shown). The particle therapy device irradiates, for example, diseased tissues (cancer) of a patient 10 with particle beams (therapeutic radioactive rays) for treatment. Particle beams are defined as ones heavier than electrons among radioactive rays, and include proton beams and heavy particle beams. Heavy particle beams are defined as ones heavier than helium atoms.

Example radiation therapy technology using particle therapy devices is cancer therapy technology by heavy particle rays. In this technology, carbon ions target the cancer lesion (affected area) with pinpoint accuracy to damage the cancer lesion while minimizing damage to normal cells.

In comparison with conventional cancer therapy using X-rays, gamma rays, or proton beams, heavy particle beams are characterized by higher ability to kill cancer lesions in cancer therapy, low radiation dose on the surface of the body of the patient 10 and a peak dose at the cancer lesion. Such characteristics can reduce the number of irradiation operations and side effects and can shorten the duration of treatment.

Although not shown in the drawing, the particle therapy device is equipped with an ion generator, an accelerator, and a beam transport line. The ion generator has a source of carbon ions, which are charged particles, and generates particle beams of the carbon ions. The accelerator has an annular shape in plan view and accelerates the particle beams generated by the beam generator. The beam transport line transports the particle beams accelerated by the accelerator.

The particle therapy device is also equipped with a rotating gantry 12 (FIG. 1). The patient 10 is positioned to be irradiated with the particle beams guided by the beam transport line in the rotating gantry 12.

As shown in FIG. 1, the rotating gantry 12 is a large apparatus having a cylindrical shape. The rotating gantry 12 is installed such that the rotational axis Q at the center of the cylinder extends in the horizontal direction. The rotating gantry 12 can rotate circumferentially around the rotational axis Q.

A radioactive ray emitter 17 is installed at the periphery of the rotating gantry 12 to radiate the particle beams (therapeutic radioactive rays) toward the patient 10. The radioactive ray emitter 17 is fixed to the inner surface of the rotating gantry 12. The particle beams are radiated from the radioactive ray emitter 17 in a direction perpendicular to the rotational axis Q.

A treatment table 11 is provided inside the rotating gantry 12. The patient 10 lies down on the treatment table 11. The rotating gantry 12 surrounds the treatment table 11 and rotates around the treatment table 11.

The treatment table 11 is fixed to the floor of a stationary treatment room (not shown). This indicates that the position of the treatment table 11 does not change during the rotation of the rotating gantry 12 and radioactive ray emitter 17.

The rotational axis Q of the rotating gantry 12 is adjusted to align with the position of the patient 10 lying on the treatment table 11. The treatment table 11 is movable with the patient 10 on it. This movement of the treatment table 11 allows the patient 10 to move to a position of radiating particle beams for alignment. The particle beams can thus arrive at the appropriate site, such as the diseased tissue of the patient 10. After positioning, the radioactive ray emitter 17 irradiates the patient 10 lying on the treatment table 11 with radioactive rays.

Rotation of the rotating gantry 12 enables the radioactive ray emitter 17 to rotate around the stationary patient 10 (rotational axis Q). For example, the radioactive ray emitter 17 can rotate clockwise (rightward) or counterclockwise (leftward) by about 180 degrees around the patient 10. The particle beams can then be radiated from any direction around the patient 10 (360 degrees). In other words, the rotating gantry 12 is an apparatus that can change the radiation direction of the particle beams to the patient 10. This makes it possible to irradiate the affected area with the particle beams from the appropriate direction with higher precision while reducing the burden on the patient 10.

The particle beams, which pass through the body of the patient 10, undergoes a resistance approximately inversely proportional to the square of its velocity, loses kinetic energy accompanying a decrease in velocity, and abruptly stops when it reaches a certain velocity. This stopping point of the particle beams is called the Bragg peak, where high energy is emitted. The particle therapy device can match the Bragg peak to the location of the diseased tissues (affected area) of the patient 10 to kill only the diseased tissue while minimizing damage to normal tissues.

The X-ray generator 13 and radiographic unit 14 are fixed to the rotating gantry 12. The X-ray generator 13 and radiographic unit 14 rotate with the rotating gantry 12 to irradiate the patient 10 with X-rays and capture X-ray transmitted images 29.

Figure 5:
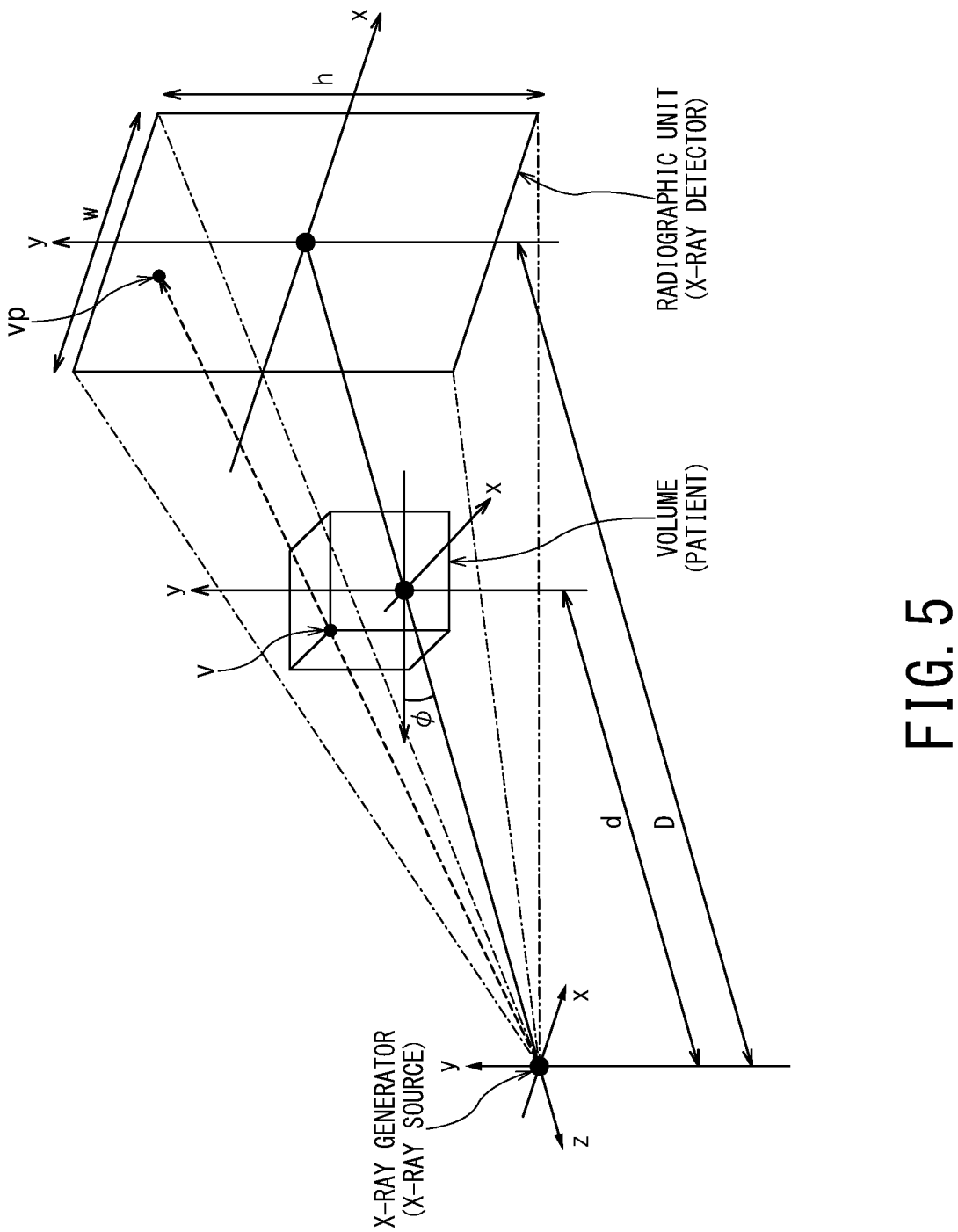
FIG. 5 is an illustrative view of the concept of coordinate conversion from the coordinates of a patient to the coordinates of the radiographic unit.

Now referring to FIG. 5, tomography (CT imaging) will be explained. Two types of X-rays are used in tomography:

fan beams, which diffuse in a fan shape, and cone beams, which diffuse in a cone shape. The rotating gantry 12 performs tomographic imaging with cone-beam X-rays. In the case of use of cone-beam X-rays, the following series of matrix equations are used in the coordinate transformation from the coordinates V (x, y, z) of the patient 10 to the coordinates $V_P$ ($x_p$, $y_p$, $z_p$) of the radiographic unit 14 (X-ray detector):

$$E \times P \times T \times R \times V = V_P$$

These matrices can be written by Expression 1.

$$\begin{bmatrix} \dfrac{N_w}{2} & 0 & 0 & \dfrac{N_w}{2} \\ 0 & \dfrac{N_h}{2} & 0 & \dfrac{N_h}{2} \\ 0 & 0 & 1 & 1 \\ 0 & 0 & 0 & 1 \end{bmatrix} \begin{bmatrix} \dfrac{2D}{w} & 0 & 0 & 0 \\ 0 & \dfrac{2D}{h} & 0 & 0 \\ 0 & 0 & \dfrac{-(f+n)}{f-n} & \dfrac{-2fn}{f-n} \\ 0 & 0 & -1 & 0 \end{bmatrix} \quad \text{(Expression 1)}$$

$$\begin{bmatrix} 1 & 0 & 0 & 0 \\ 0 & 1 & 0 & 0 \\ 0 & 0 & 1 & -d \\ 0 & 0 & 0 & 1 \end{bmatrix} \begin{bmatrix} \cos\phi & 0 & -\sin\phi & 0 \\ 0 & 1 & 0 & 0 \\ \sin\phi & 0 & \cos\phi & 0 \\ 0 & 0 & 0 & 1 \end{bmatrix} \begin{bmatrix} x \\ y \\ z \\ 1 \end{bmatrix} = \begin{bmatrix} x_p \\ y_p \\ z_p \\ w_p \end{bmatrix}$$

The rotation matrix R rotates the volume (patient 10) coordinate system rotated counterclockwise by an angle φ around the y-axis. The parallel shift matrix T shifts the volume coordinate system by a distance d along the direction of X-ray radiation (z-axis) to the negative side. These two rotation matrices R and T map from the volume coordinate system to the X-ray source coordinate system. The perspective projection matrix P is determined by the position D of the X-ray generator 13 (X-ray source) and the dimensions w and h of the radiographic unit 14 (X-ray detector). The perspective projection matrix P defines the projected range of cone-beam X-rays as the shape of the frustum. Parameters n and f of the perspective projection matrix P represent the distances from the X-ray source to the respective far and near clipping planes of the frustum. Furthermore, the coordinate transformation matrix E forms the coordinate $V_P$ of the radiographic unit 14 with respect to the coordinate V of the patient 10.

The X-ray generator 13 and the radiographic unit 14 installed in the rotating gantry 12 rotates around the patient 10 while capturing X-ray images to acquire image data based on the calculation using the aforementioned matrix equation. Based on this image data, a three-dimensional reconstructed image (CT image) is generated.

The rotation rate of the rotating gantry 12, however, is about 1 to 2 minutes per revolution, which is too long for the breathing cycle, which is about 3 to 4 seconds of the patient 10. The imaging targets (affected areas and organs) are moved in conjunction with the breathing of the patient 10 during one revolution of the rotating gantry 12 for shooting. For such a reason, conventional techniques fail to capture highly accurate reconstructed images. In contrast, the system of the embodiment can solve such problems. In particular, it can improve the accuracy of the positioning of the patient 10, which is performed by comparing the reference image acquired using a predetermined CT imaging device (not shown) at a time of treatment regimen with the reconstructed image acquired using the rotating gantry 12 immediately before treatment.

Before the treatment regimen, a CT image of the patient 10 is taken, and then, the area to be irradiated, the direction of irradiation, and the irradiation dose are determined with reference to the pattern of the affected area in the image. Since this treatment regimen process takes a number of days, the patient 10 will be irradiated with particle beams several days after the CT images are taken for the treatment regimen. Because of this several-days gap, the affected area may be displaced when the patient 10 is positioned just prior to treatment. It is necessary to distinguish whether this misalignment is due to differences in the conditions of the patient 10 on that day or due to normal respiratory motion. The imaging control system 1 of the embodiment is accordingly used.

Figure 2:
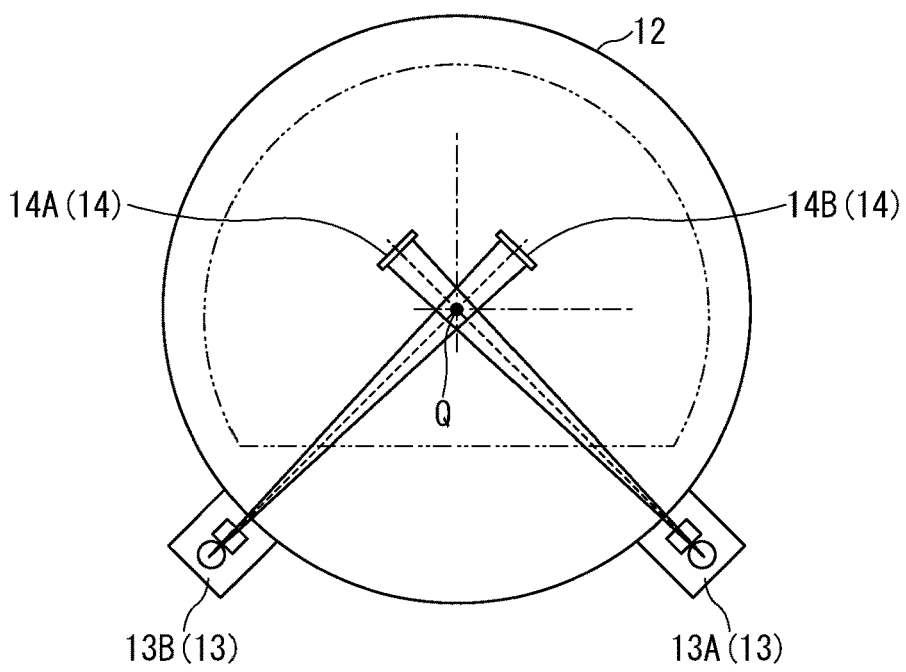
FIG. 2 is an illustrative view of a configuration of an X-ray generator and a radiographic unit.

As shown in FIGS. 1 and 2, the imaging control system 1 includes the treatment table 11, rotating gantry 12, X-ray generator 13, and radiographic unit 14.

The X-ray generator 13 consists of a first X-ray generating unit 13A and a second X-ray generating unit 13B. These first and second X-ray generating units 13A and 13B are installed at the edge of the rotating gantry 12 at an angle of 90 degrees apart from each other around the rotational axis Q of the rotating gantry 12.

The first and second X-ray generating units 13A and 13B are, for example, X-ray tubes that emit X-rays (photographic radioactive rays) toward the patient 10 placed on the treatment table 11 during revolution of the rotating gantry 12.

The radiographic unit 14 includes a first radiographic segments 14A and a second radiographic segments 14B. The first radiographic segment 14A is disposed at a position 180 degrees distant from the first X-ray generating unit 13A around the rotational axis Q of the rotating gantry 12. This first radiographic segment 14A is located adjacent to the radioactive ray emitter 17 and is in cooperation with the first X-ray generating unit 13A. The second radiographic segment 14B is disposed at a position 180 degrees distant from the second X-ray generating unit 13B about the rotational axis Q of the rotating gantry 12. This second radiographic segment 14B is positioned adjacent to the radioactive ray emitter 17 and is in cooperation with the second X-ray generating unit 13B.

During the rotation of the rotating gantry 12, X-rays emitted from the first X-ray generating unit 13A transmit through the patient 10. The first radiographic segment 14A outputs image data including multiple two-dimensional X-ray images taken through these transmitted X-rays. Also, during rotation of the rotating gantry 12, X-rays emitted from the second X-ray generating unit 13B transmit through the patient 10. The second radiographic segment 14B outputs image data including multiple two-dimensional X-ray images taken through these transmitted X-rays.

Figure 3:
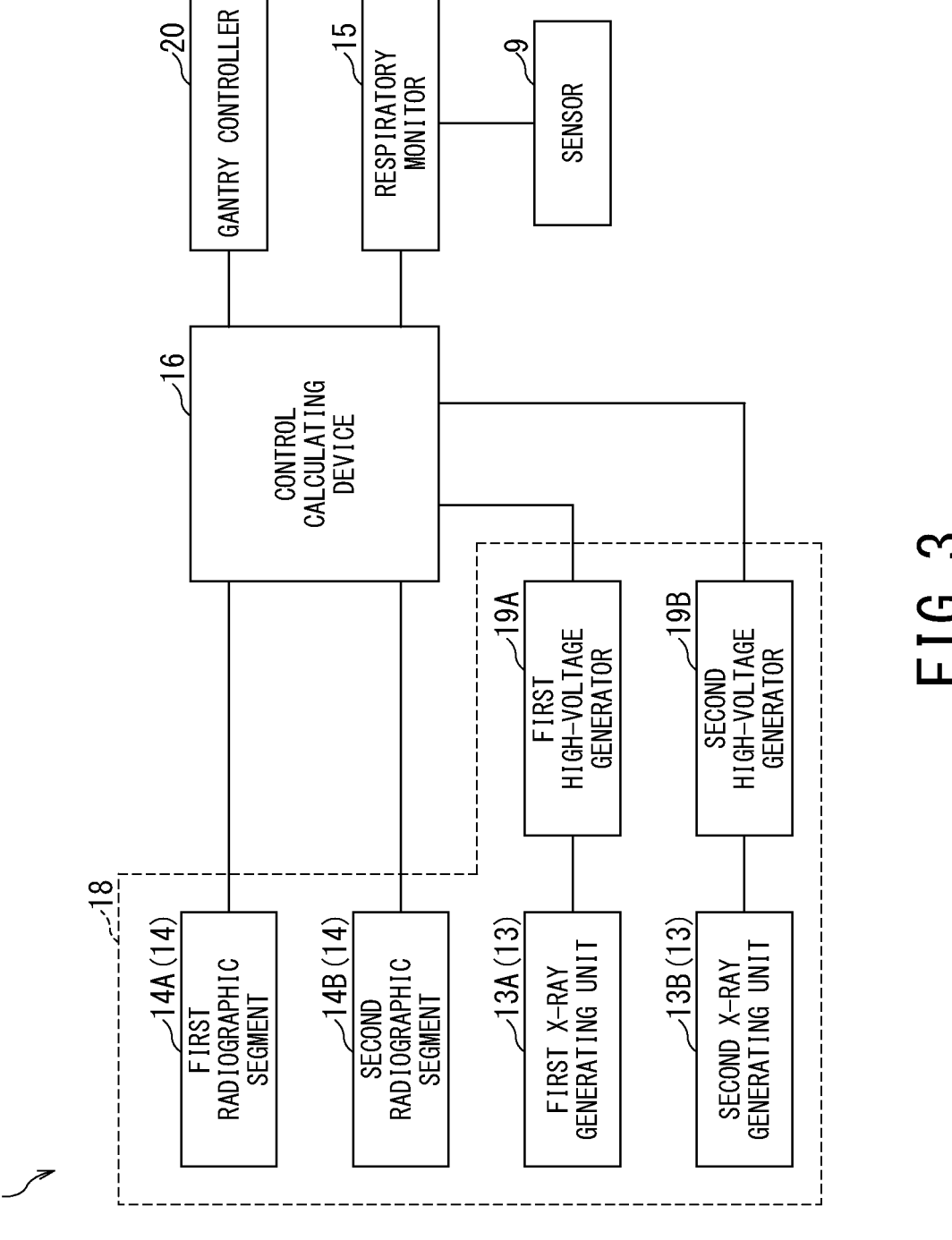
FIG. 3 is a block diagram of the imaging control system.

The imaging control system 1 includes a respiratory monitor 15 (see FIG. 3). The respiratory monitor 15 has, for example, a sensor 9 installed on the treatment table 11. The sensor 9 measures an amount of respiratory motion that is reflected on the body surface of the patient 10 lying on the treatment table 11. For example, the sensor 9 radiates sensing rays, such as infrared, laser, ultrasound, or millimeter waves, onto the chest or abdomen of the patient 10 and measures the amount of respiratory motion based on the reflections of the sensing rays. The sensor 9 may also radiate X-rays, ultrasound, or magnetism onto the patient 10 and measure changes in the positions of structures in the body.

The respiratory monitor 15 acquires respiratory data indicating the respiratory motion of the patient 10 from the sensor 9 for monitoring of the respiratory motion of the patient 10. In other words, the monitor acquires information indicating periodic fluctuations in the body of the patient 10 due to respiration.

The system configuration of the imaging control system 1 will now be described with reference to the block diagrams shown in FIGS. 3 to 4. The imaging control system 1 is equipped with a respiratory monitor 15, a control calculating device 16, an X-ray imaging device 18, and a gantry controller 20.

The X-ray generator 13 and the radiographic unit 14 are included in the X-ray imaging device 18 of the first embodiment. In other words, at least a part of the X-ray imaging device 18 rotates with the rotating gantry 12 and radiates X-rays toward the patient 10 to capture X-ray images. Furthermore, a first high-voltage generator 19A that generates high voltage for the first X-ray generating unit 13A and a second high-voltage generator 19B that generates high voltage for the second X-ray generating unit 13B are also included in the X-ray imaging device 18.

The control calculating device 16 of the present embodiment includes hardware resources such as a Central Processing Unit (CPU), a Read Only Memory (ROM), a Random Access Memory (RAM) and/or a Hard Disk Drive (HDD), i.e., processor and memory, and is configured as a computer in which information processing by software is achieved with the use of the hardware resources by causing the CPU to execute various programs.

The functions of the control calculating device 16 do not necessarily have to be carried by a single computer. For example, the functions of a single control calculating device 16 may be achieved using multiple computers connected to each other through a network.

The control calculating device 16 is provided with a predetermined memory, which is not specifically shown in the drawing. The memory stores various types of information necessary for execution of the method of controlling imaging.

The control calculating device 16 controls the generation of X-rays at the X-ray generator 13 and the acquisition of image data from the radiographic unit 14. Furthermore, the control calculating device 16 generates three-dimensional reconstructed images from the image data acquired by the radiographic unit 14.

In other words, the control calculating device 16 controls the first high-voltage generator 19A and the second high-voltage generator 19B. The control calculating device 16 then adjusts the timing of generation and the intensity of the X-rays radiated to the patient 10 from the first X-ray generating unit 13A and the second X-ray generating unit 13B.

The control calculating device 16 acquires image data containing the X-ray images taken by the first and second radiographic segments 14A and 14B. The image data includes a plurality of X-ray images and information on the timing of generation of X-rays when these images are taken, i.e., the timing at which the X-ray images were taken.

The control calculating device 16 sequentially retrieves the rotational angle θ of the rotating gantry 12 from the gantry controller 20 that controls the rotation of the rotating gantry 12. The control calculating device 16 also retrieves the respiration data including the respiration waveform (amount of the movement of the affected area or organ) indicating the respiratory motion of the patient 10 from the sensor 9 through the respiratory monitor 15. The respiratory waveform may be acquired in the form of a graph or in the form of numerical values arranged in chronological order.

The control calculating device 16 can generates reconstructed images and moving images (3D images). To achieve this function, the control calculating device 16 is equipped with a prestage processor 21, a respiratory waveform divider

22, an image data sorter 23, a 3D reconstructor 24, and a moving image generator 25. The functions of these device can be achieved through execution in the CPU of programs stored in the memory or HDD.

The prestage processor 21 processes image data retrieved from the radiographic unit 14 in advance. The prestage process involves, for example, noise removal by image filtering.

Figure 6:
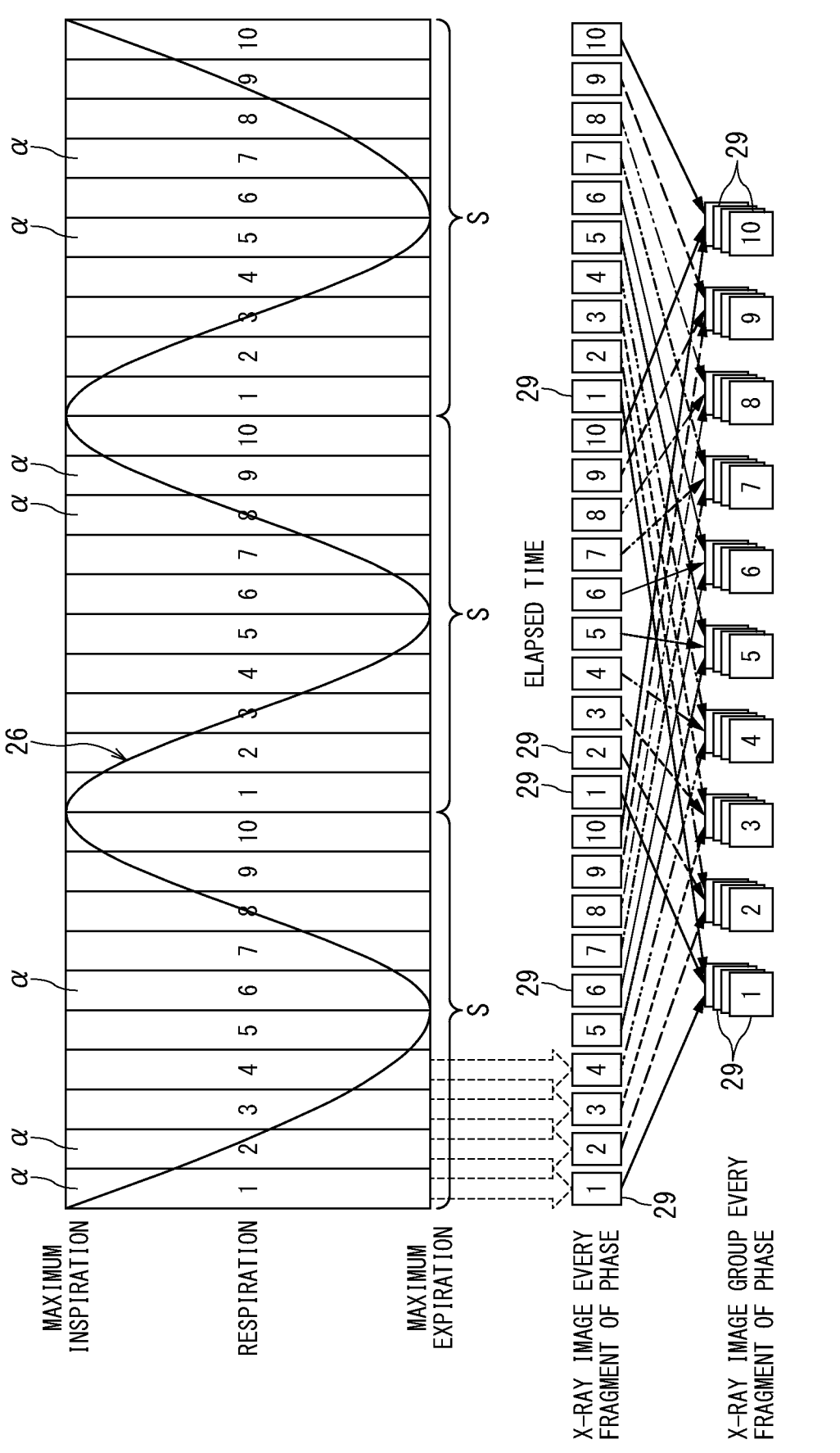
FIG. 6 is an illustration of a slicing mode of a respiratory waveform cycle into multiple fragments of phase.

As shown in FIG. 6, the first embodiment includes illustration of a fragment α of phase as a specific fragment. The respiratory waveform divider 22 slices each cycle S of the respiratory waveform 26, which indicates the amount of the respiratory motion of the patient 10 observed by the respiratory monitor 15, into several (e.g., 10) fragments α of phase. In other words, every cycle S in the respiratory waveform 26 of the respiratory motion included in the respiratory data is sliced into multiple fragments α of phase.

In FIG. 6, each of the X-ray images 29 is identified by a numeral from "1" to "10" assigned to the corresponding fragment α of phase. The same number indicates the same fragment α of phase. These numerals "1" to "10" will be described as fragment identifiers that can identify the specific fragment.

The rotating gantry 12 in the imaging control system 1 takes one to two minutes per revolution, unlike a common CT imaging system (not shown). In contrast, the cycle S of the respiratory waveform 26 in the breathing motion of the patient 10 is about three to four seconds. Multiple breaths will thus be taken during one revolution of the rotating gantry 12. One cycle S is the time from maximum inspiration through maximum expiration to next maximum inspiration.

The affected areas and organs that moves with the respiratory motion of the patient 10 will be in approximately the same position in the same fragments α of phase, for example, in the "1st" fragments α of phase and also in the "2nd" fragments α of phase in the respiratory waveform 26 of this respiratory motion.

The image data sorter 23 categorizes multiple X-ray images 29 taken in chronological order in the radiographic unit 14 by the fragment α of phase (specific fragment) determined by the respiratory waveform divider 22. The image data sorter 23 categorizes these X-ray images 29 together with the rotational angles θ of the rotating gantry 12 at the times of the respective X-ray images 29.

Thus, a data set is generated that maps each fragment α of phase of the respiratory waveform 26 to the X-ray images 29 taken by the radiographic unit 14 and the rotational angles θ of the rotating gantry 12 at the imaging times of the respective X-ray images 29.

This data set includes X-ray images 29 that are correlated with fragment identification information that can identify the specific fragment and the rotational angle θ of the rotating gantry 12 at the time of imaging. In this way, the X-ray images 29 can readily be managed and the subsequent process of generating reconstructed images can be readily performed. The control calculating device 16 has an image management table that manages multiple data sets.

The 3D reconstructor 24 rebuilds multiple data sets categorized every identical fragment α of phase of the respiratory waveform 26 by the image data sorter 23 to generate a 3D reconstructed image for each fragment α of phase.

The moving image generator 25 reconstructs multiple X-ray images 29 (a group of X-ray images) categorized every fragment α of phase contained in the data set based on the rotational angles θ of the rotating gantry 12 at the time of imaging to generate a three-dimensional reconstructed image.

Specifically, multiple 3D-reconstructed images generated by the 3D reconstructor 24 for the respective fragments α of phase of the respiratory waveform 26 are categorized to be integrated along the time series of the phases of the respiratory waveform 26 to generate a moving image with a time axis. In a word, a three-dimensional animated image is generated.

Thus, the control calculating device 16 sequentially performs the aforementioned processes in the respiratory waveform divider 22, the image data sorter 23, the 3D reconstructor 24, and the moving image generator 25 to generate reconstructed images and 3D animated images or moving images.

The control calculating device 16 outputs a moving image that can play back the multiple reconstructed images along the time axis of the respiratory waveform 26. In this way, the moving image can be used to observe the state of the patient 10, which changes in chronological order in response to respiration.

The moving images include not only those played back corresponding to one average cycle S of respiration and those played back in chronological order but also those played back in the reverse direction (reverse playback) of the chronological order.

Figure 4:
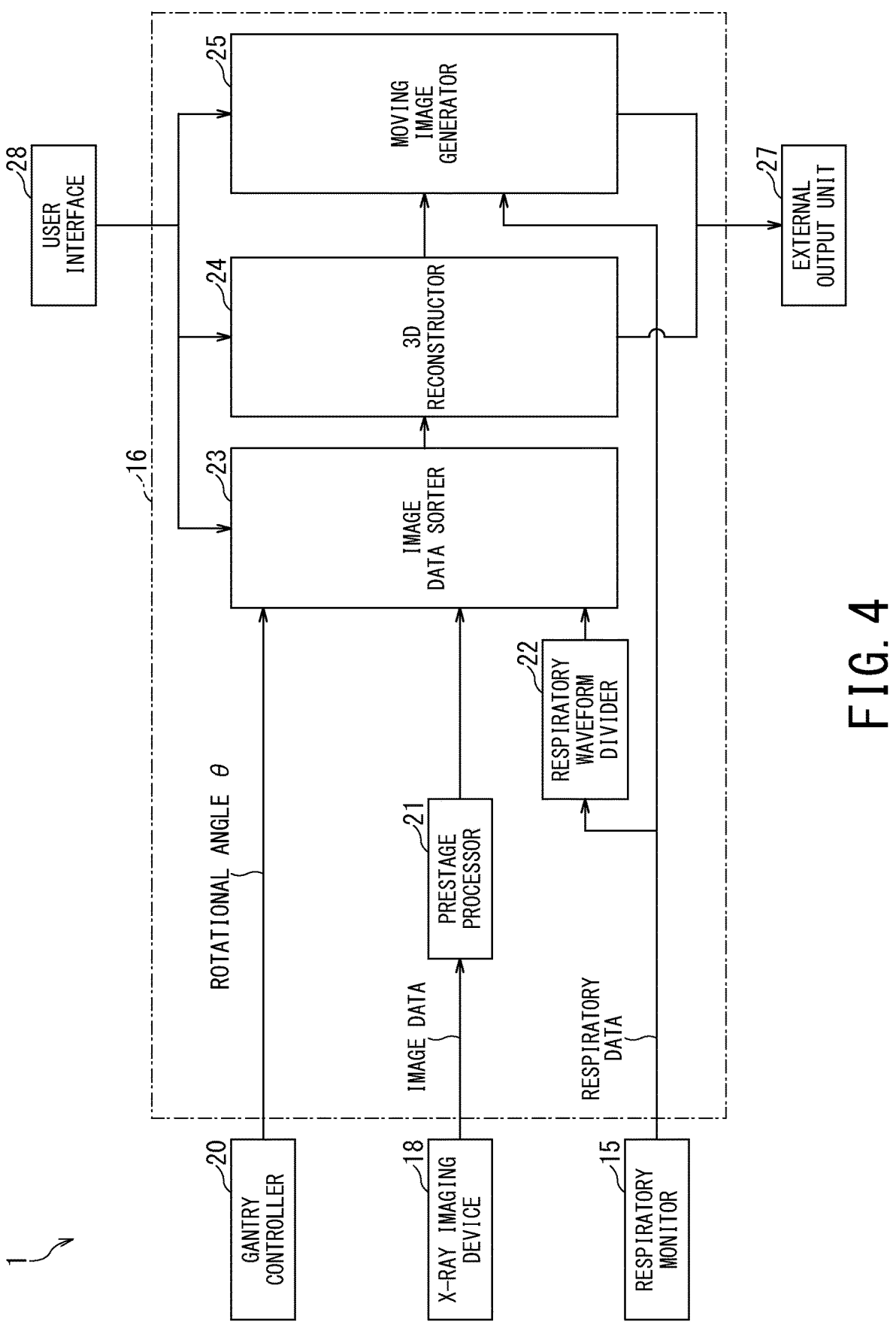
FIG. 4 is a block diagram of a control calculating device.

The images generated by the control calculating device 16 are outputted to an external output unit 27 (FIG. 4). This external output unit 27 consists, for example, of a display capable of showing images. The external output unit 27 may be separated from or integrated into the control calculating device 16. Alternatively, the external output unit 27 may be a display provided by another computer connected via a network. The external output unit 27 may also be a printer that prints information on paper media.

The control calculating device 16 may be connected to a predetermined user interface 28. The user interface 28 may, for example, be in the form of a program that runs simultaneously inside the control calculating device 16. Alternatively, the user interface 28 may be in the form of a program that runs inside a different computer other than the control calculating device 16 and sends and receives information to and from the control calculating device 16 through a network.

The method of controlling imaging, which is a process executed by the imaging control system 1, will now be described with reference to the flowchart in FIG. 7.

In step S1, the image data sorter 23 (FIG. 4) of the control calculating device 16 retrieves a rotational angle θ indicating the rotated position of the rotating gantry 12 (FIG. 1) from the gantry controller 20 that controls the rotating gantry 12 rotating around the patient 10.

In step S2, the prestage processor 21 (FIG. 4) of the control calculating device 16 acquires image data from the X-ray imaging device 18 rotating with the rotating gantry 12, which image data including multiple two-dimensional X-ray images 29 is taken by irradiating the patient 10 with X-rays.

In step S3, the respiratory waveform divider 22 (FIG. 4) and the moving image generator 25 (FIG. 4) of the control calculating device 16 retrieves respiratory data from the respiratory monitor 15 that watches the respiratory motion of the patient 10 and outputs the respiratory data indicating respiratory motion.

In step S4, the respiratory waveform divider 22 (FIG. 4) of the control calculating device 16 slices each cycle S in the respiratory waveform 26 (FIG. 6) of the respiratory motion contained in the respiratory data into multiple fragments α of phase.

In step S5, the image data sorter 23 (FIG. 4) of the control calculating device 16 categorizes the X-ray images 29 (FIG. 6) contained in the image data every fragment α of phase.

In step S6, the moving image generator 25 (FIG. 4) of the control calculating device 16 reconstructs the multiple X-ray images 29 (FIG. 6) categorized every fragment α of phase based on the rotational angle θ of the rotating gantry 12 during imaging to generate a three-dimensional reconstructed image.

The imaging control system 1 then terminates the method of controlling the imaging. These steps are mere a part of this method of controlling imaging, and the method may further include any other step.

In the case that the respiratory waveform 26 (FIG. 6) of the respiratory motion of the patient 10 is regular in the first embodiment, the affected areas and organs of the patient 10 reside at the same positions when the same fragment of phase in the respiratory waveform 26. Accordingly, the control calculating device 16 reconstructs the X-ray images 29 taken by the radiographic unit 14 every identical fragment α of phase in the respiratory waveform 26 of the respiratory motion of the patient 10 into a reconstructed image. As a result, the positions of the affected areas and organ, which move with the respiratory motion of the patient 10, can be accurately determined by the reconstructed image. As a result, the fragment of phase of the respiratory waveform 26 of the patient 10 who is to be irradiated with the particle beams (therapeutic radiation) can be clarified on radiation therapy, achieving highly accurate radiation therapy.

The control calculating device 16 reconstructs the X-ray images 29 taken by the radiographic unit 14 every identical fragment α of phase in the respiratory waveform 26 of the respiratory motion of the patient 10 to generate reconstructed images and by arranging the images in chronological order of the phase of the respiratory waveform 26 and integrating these reconstructed images every fragment α of phase. The reconstructed images are output as three-dimensional animated images (moving images) with a time axis. Since the state of the moving affected area and organs accompanied with the respiratory motion of the patient 10 can be observed in three dimensions, the location of the moving affected area and organs accompanied with the respiratory motion of the patient 10 can be more accurately determined. As a result, the fragment of phase of the respiratory waveform 26 of the patient 10 to be irradiated with particle beams can be more accurately determined in performing radiation therapy, resulting in more accurate radiation therapy.

In the control calculating device 16, the respiratory waveform divider 22 slices the cycle S in the respiratory waveform 26 of the respiratory motion of the patient 10 into multiple fragments α of phase, and the image data sorter 23 and the 3D reconstructor 24 generate a reconstructed image for each fragment α of phase. Furthermore, the moving image generator 25 generates a three-dimensional animated image (moving image) with a time axis from these reconstructed images, which simplifies the algorithm of the control calculating device 16. Accordingly, the imaging control system 1 implementing this control calculating device 16 can be easily constructed.

The X-ray imaging device 18 takes images before irradiating the patient 10 with the particle beams (therapeutic radiation), and the control calculating device 16 generates reconstructed images to be used for matching with the previously acquired reference images for treatment regimen. In this way, the reconstructed image can be used to accurately determine the condition of the patient 10 on positioning the patient 10 just prior to irradiating the patient 10 with the particle beams.

(Second embodiment) With reference to FIG. 8, the second embodiment will now be described. The same numerals or symbols will be used for the same constituents as those shown in the first embodiment, without redundant description. Since the hardware configuration of the imaging control system 1 of the second embodiment is the same as that of the first embodiment, FIGS. 1 to 4 are referred to as appropriate. The flowchart in FIG. 7 will also be referred to as appropriate.

Similar to the first embodiment described above, the control calculating device 16 (FIG. 4) of the second embodiment controls the generation of X-rays by the X-ray generator 13 (FIG. 3), the retrieval of image data from the radiographic unit 14 (FIG. 3), the retrieval of the rotational angle θ from the gantry controller 20 (FIG. 4), and the retrieval of respiration data from the respiratory monitor 15 (FIG. 4). Unlike the first embodiment, the fragment β of amplitude is exemplified as the specific fragment in the second embodiment.

Figure 8:
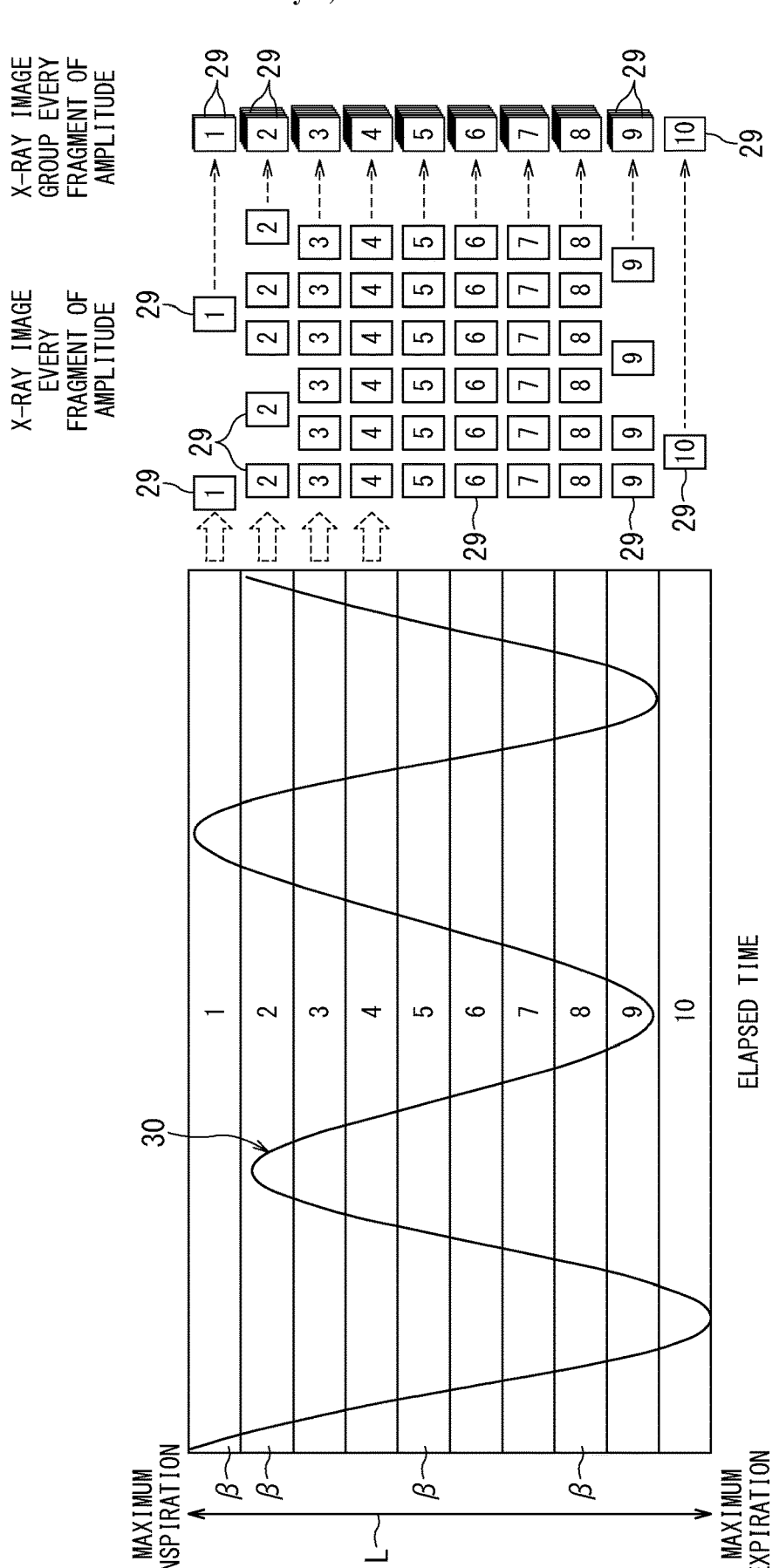
FIG. 8 is an illustration of a slicing mode of the respiratory waveform of a second embodiment into multiple fragments of amplitude.

As shown in FIG. 8, the respiratory waveform 30 of the respiratory motion of the patient 10 may be irregular varying with each breath in the maximum inspiration or expiration, for example. Even in such cases, when the affected areas and organs are in the same position in the case that they reside in the same fragment β of amplitude.

Based on this fact, the respiratory waveform divider 22 of the second embodiment slices each amplitude L in the respiratory waveform 30 that is the amount of the respiratory motion of the patient 10 observed by the respiratory monitor 15 into a multiple (e.g., ten) fragments β of amplitude. In other words, each amplitude L in the respiratory waveform 30 of the respiratory movement included in the respiratory data is sliced into multiple fragments β of amplitude.

In the example in FIG. 8, a numeral from "1" to "10" is assigned to the respective fragments β of amplitude for the X-ray images 29. The same numeral indicates the same fragment β of amplitude. These numerals "1" to "10" are described as fragment identifying information that can identify the specific fragment.

The affected areas and organs that move with the respiratory motion of the patient 10 will be in an approximately identical position in the corresponding fragment β of amplitude in the respiratory waveform 30 of this respiratory motion, for example, at the corresponding position in the "1st" fragments β of amplitude and at the corresponding position in the "2nd" fragment β of amplitude.

The control calculating device 16 stores in advance information on a divisional region and a number of divisions for slicing each amplitude L into multiple fragments β of amplitude (specific fragments). In this way, while image data is acquired during rotation of the rotating gantry 12, these image data can be categorized every fragment β of amplitude.

For example, the respiratory waveform divider 22 preliminarily stores information on the divisional region from maximum inspiration to maximum expiration and the number of divisions on the amplitude L to be sliced, in order to slice each amplitude L in the respiratory waveform 30 of the respiratory motion of the patient 10 into multiple fragments β of amplitude. In other words, after one rotation of the rotating gantry 12, the divisional region and the number of divisions of the amplitude L to be sliced are determined in advance, rather than determination of the divisional region and the number of divisions based on the distribution of the respiratory waveform 30 of the respiratory motion of the patient 10.

The image data sorter 23 categorizes multiple X-ray images 29 taken in chronological order in the radiographic unit 14 every fragment β of amplitude (specific fragments) sliced by the respiratory waveform divider 22. The image data sorter 23 categorizes the X-ray images 29 together with the rotational angle θ of the rotating gantry 12 at the time of taking each of these X-ray images 29.

Thus, a data set is generated that maps the X-ray images 29 taken by the radiographic unit 14 to the rotational angle θ of the rotating gantry 12 at the time the respective X-ray images 29 are taken, every fragment β of amplitude of the respiratory waveforms.

The 3D reconstructor 24 reconstructs multiple data sets categorized every fragment β of amplitude of the respiratory waveform 30 at the image data sorter 23 to generate a 3D reconstructed image every fragment β of amplitude.

The control calculating device 16 then determines whether the acquired image data is appropriate for generating the reconstructed image, and rejects at least some of the image data that is determined to be inappropriate. Such a procedure can ensure the accuracy of the reconstructed image produced every fragment β of amplitude (specific fragment).

For example, the 3D reconstructor 24 determines whether the X-ray images (X-ray image group) 29 categorized by the fragment β of amplitude are inappropriate on generation of the reconstructed image. An inappropriate case is that, for example, the image data includes an insufficient number of X-ray images 29 to generate a reconstructed image. If it is determined to be inappropriate, at least a portion of the image data is discarded. This disposal ensures the accuracy of the reconstructed images generated every fragment β of amplitude.

In the case of classification of X-ray images 29 every fragment β of amplitude, which is a division of the amplitude L, of the respiratory waveform 30, no X-ray image 29 can be acquired in the fragment β of amplitude near the maximum inspiration or maximum expiration, in particular. In such a fragment β of amplitude, a sufficient number of X-ray images 29 cannot be acquired for the generation of reconstructed images during one rotation of the rotating gantry 12.

The middle position of the respiratory waveform 30 may shift during one rotation of the rotating gantry 12. In such a case, X-ray images 29 can be acquired (categorized) at the start of imaging but then cannot be acquired in a fragment β of amplitude close to the maximum amplitude of the respiratory waveform 30, resulting in acquisition of an insufficient number of X-ray images 29 for generation of the reconstructed image.

If the number of X-ray images 29 categorized into a predetermined fragment β of amplitude during one rotation of the rotating gantry 12 does not reach the minimum number of images required to generate a reconstructed image, the 3D reconstructor 24 does not generate a reconstructed image for the fragment β of amplitude. It is noted that the minimum number of images is stored in advance in the 3D reconstructor 24.

Even if the number of X-ray images 29 categorized in each fragment β of amplitude satisfies the minimum number of images, the 3D reconstructor 24 may abandon generation of reconstructed images in the case of uneven numbers of X-ray images 29 among the fragments β of amplitude. For example, all image data acquired at that time may be discarded without generation of the reconstructed image, depending on the image data acquired during one rotation of the rotating gantry 12.

The angular range (360 degrees) of one rotation of the rotating gantry 12 is divided into several equally segmented angular ranges. The X-ray images 29 are categorized every fragment β of amplitude in each segmented angular range. If the number of X-ray images 29 categorized into every fragment of amplitude is not equal, for example, if the variation in the number of images is not within 20%, all the image data acquired at that time may be discarded without generation of the reconstructed image in all the fragments β of amplitude from the image data acquired during this rotation of the rotating gantry 12.

The moving image generator 25 sequentially sorts and integrate the multiple reconstructed images generated by the 3D reconstructor 24 every fragment β of amplitude of the respiratory waveform 30 from the maximum inspiration to the maximum expiration of the respiratory waveform 30 to generate a three-dimensional animated image (moving image) that changes sequentially between the maximum inspiration and the maximum expiration of the respiratory waveform 30. Alternatively, the multiple reconstructed images may be sequentially categorized and integrated from the maximum expiration to the maximum inspiration of the respiratory waveform 30 to generate a three-dimensional animated image (moving image).

Thus, the control calculating device 16 performs the aforementioned processes in the respiratory waveform divider 22, the image data sorter 23, the 3D reconstructor 24, and the moving image generator 25 in sequence to generate reconstructed images and 3D animated or moving images.

The control calculating device 16 outputs a moving image that can playback multiple reconstructed images from one side of the maximum inspiration and maximum expiration to the other side of the respiratory waveform 30. In this way, the moving image can be used to confirm the state of the patient 10, which changes sequentially between the maximum inspiration and the maximum expiration.

Figure 7:
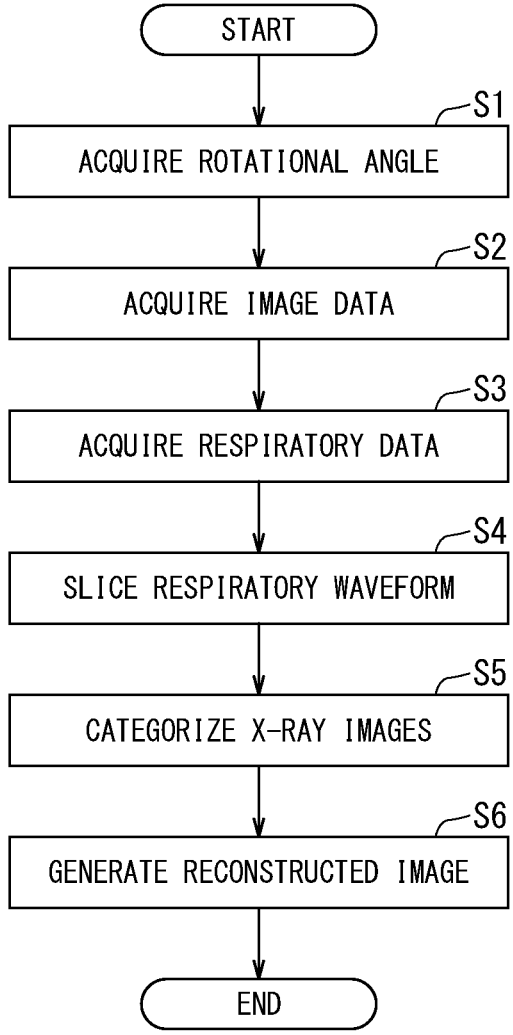
FIG. 7 is a flowchart showing a method of controlling imaging.

In the flow chart on the method of controlling imaging in FIG. 7, the second embodiment is different from the first embodiment in steps S4 to S6, but identical to the first embodiment in steps S1 to S3.

For example, in step S4, the respiratory waveform divider 22 (FIG. 4) of the control calculating device 16 slices the amplitude L in the respiratory waveform 30 (FIG. 8) of the respiratory motion included in the respiratory data into multiple fragments β of amplitude.

In step S5, the image data sorter 23 (FIG. 4) of the control calculating device 16 categorizes the X-ray images 29 (FIG. 8) included in the image data every fragment β of amplitude.

In step S6, the moving image generator 25 (FIG. 4) of the control calculating device 16 reconstructs the multiple X-ray images 29 (FIG. 8) categorized every fragment β of amplitude based on the rotational angle θ of the rotating gantry 12 during imaging to generate a three-dimensional reconstructed image.

Even if the respiratory waveform 30 (FIG. 8) of the respiratory motion of the patient 10 is irregular as described above, the affected areas and organs of the patient 10 reside in the same position in the same fragment β of amplitude of the amplitude L of this respiratory waveform 30. Thus, in the case that the respiratory waveform 30 is particularly irregular, the control calculating device 16 can reconstructs the image data including the X-ray image 29 taken by the radiographic unit 14 every identical fragment β of amplitude in the respiratory waveform 30 of the respiratory motion of the patient 10 to generate a three-dimensional reconstructed image.

In the second embodiment, the occurrence of artifacts such as shadows in the reconstructed image can be reduced. As a result, the positions of affected areas and organs that moves with the respiratory motion of the patient 10 can be accurately identified in the reconstructed image. In addition, the fragment of phase position of the respiratory waveform 30 of the patient 10 can be clearly determined on irradiation with the particle beams (therapeutic radiation) ion radiation therapy, thus enabling highly accurate radiation therapy.

The control calculating device 16 reconstructs the X-ray image 29 taken at the radiographic unit 14 every identical fragment β of amplitude in the respiratory waveform 30 of the respiratory motion of the patient 10 to generate a reconstructed image, sort these reconstructed images every fragment β of amplitude in the respiratory waveform 30 from one side of the maximum inspiration and the maximum expiration to the other side, and outputs a three-dimensional animated image (moving image) that sequentially moves between the maximum inspiration and the maximum expiration. Since three-dimensional movement of the affected areas and organs accompanied with the respiratory motion of the patient 10 can be observed, the positions of the affected areas and organs that moves accompanied with the respiratory motion of the patient 10 can be determined more precisely. As a result, the phase position of the respiratory waveform 26 of the patient 10 to be irradiated with the particle beams can be distinctly determined on radiation therapy, resulting in more accurate radiation therapy.

If the 3D reconstructor 24 of the control calculating device 16 determines that the X-ray images 29 categorized every fragment β of amplitude in the respiratory waveform 30 of the respiratory motion of the patient 10 are inappropriate for generating a reconstructed image, at least part of the image data is discarded without generation of a reconstructed image from those X-ray images 29. As a result, the 3D reconstructor 24 can eliminate the time for wasted data processing, which allows the reconstructed image to be readily generated in the other fragments β of amplitude.

The respiratory waveform divider 22 of the control calculating device 16 preliminarily stores information on the divisional region and the number of multiple fragments β of the amplitude L in the respiratory waveform 30 of the respiratory motion of the patient 10. Thus, the control calculating device 16 can acquire image data from the radiographic unit 14 during rotation of the rotating gantry 12 and sort the X-ray images 29 contained in the image data with the rotational angle θ of the rotating gantry 12 by the respiratory waveform divider 22 every fragment β of amplitude at the imaging. Since the X-ray images 29 are categorized during the rotation of the rotating gantry 12, the reconstructed images can be generated immediately after image data acquisition from the radiographic unit 14.

(Third embodiment) The third embodiment will now be described with reference to FIGS. 9 through 13. The same reference numerals and symbols will be used for the same constituents as those shown in the above-described embodiments without redundant description. FIGS. 1, 2, 3, 6, and 8 will be cited as appropriate.

The third embodiment can be combined with either the first embodiment, in which the specific fragment is illustrated as the fragment α of phase (FIG. 6), or the second embodiment, in which the specific fragment is illustrated as the fragment β of amplitude (FIG. 8). In the following description, the form in which the specific fragment is the fragment α of phase will be illustrated as an example.

As in the first embodiment, the X-ray imaging device 18 of the third embodiment has at least two (first and second) radiographic units 14 (FIG. 3) that capture X-ray images 29 (FIG. 6) at multiple imaging angles accompanied with the rotation of the rotating gantry 12 (FIG. 1).

The imaging angle corresponds to the rotational angle θ of the rotating gantry 12 when the X-ray image 29 was taken and indicates the angular position of the first and second radiographic segments 14A and 14B when the first and second radiographic segments 14A and 14B are rotated around the patient 10 in the center.

The first radiographic segment 14A and the second radiographic segment 14B are disposed at circumferentially 90 degrees apart around the rotational axis Q of the rotating gantry 12, i.e., the patient 10. Accordingly, the angle defined by the imaging directions of the first and second radiographic segments 14A and 14B is 90 degree. This angle is a fixed value.

The imaging direction is the direction of the straight line extending from the first X-ray generating unit 13A to the first radiographic segment 14A and is also the direction of the straight line extending from the second X-ray generating unit 13B to the second radiographic segment 14B.

Figure 9:
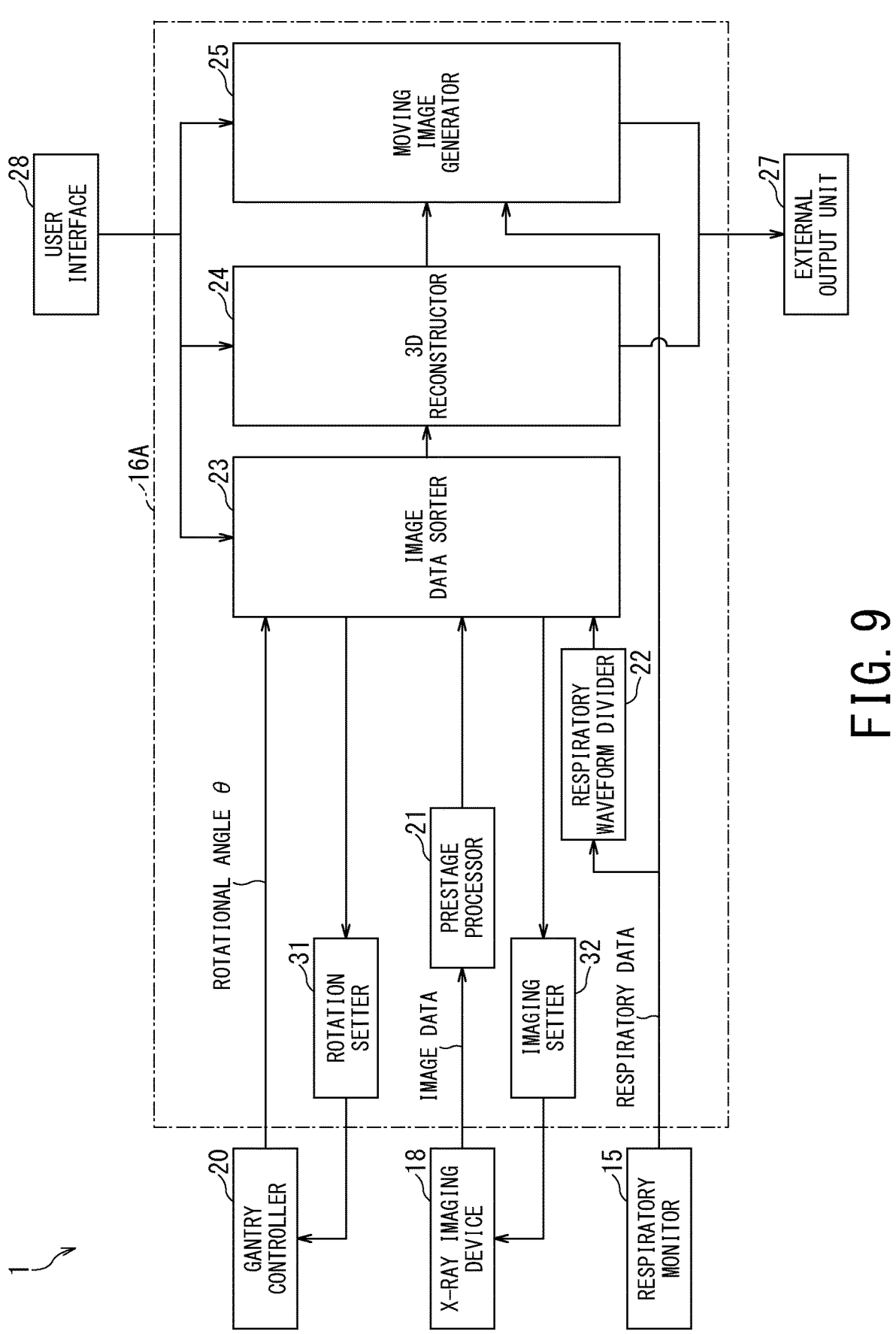
FIG. 9 is a block diagram of the control calculating device of a third embodiment.

With reference to FIG. 9, the control calculating device 16A in the third embodiment has a rotation setter 31 and an imaging setter 32, in addition to the aforementioned configuration of the prestage processor 21, the respiratory waveform divider 22, the image data sorter 23, the 3D reconstructor 24, and the moving image generator 25.

The rotation setter 31 is connected to the gantry controller 20 and establishes the rotational angle and the rotational speed of the rotating gantry 12. The imaging setter 32 is connected to the X-ray imaging device 18 and establishes the imaging conditions for X-ray images 29.

A control mode of the rotational speed of the rotating gantry 12 includes control of the rotational speed of the rotating gantry 12 in response to the breathing of the patient 10. The rotational speed of the rotating gantry 12 may be controlled without matching the breathing of the patient 10. For example, the rotational speed of the rotating gantry 12 may be kept constant each time and the timing of X-ray imaging may be adjusted in response to the breathing of the patient 10. The pattern of the rotational speed of the rotating gantry 12, including a change between high and low rotational speeds of the rotating gantry 12, may be constant each time, and the timing of the X-ray imaging may be adjusted to match the respiration of the patient 10. Instead of the adjustment of the rotational speed of the rotating gantry 12 to the breathing pattern unique to each patient 10, for example, the rotational speed of the rotating gantry 12 may be controlled to match the number of breaths per unit time (average timing of breathing) of multiple (common) patients 10.

The establishments by the rotation setter 31 and the imaging setter 32 are performed in accordance with the classification mode of the X-ray images 29 in the image data sorter 23. These establishments may be preliminarily performed before the acquisition of the X-ray image 29 or may be performed as appropriate during the acquisition of the X-ray image 29.

In the X-ray imaging device 18 of the third embodiment, the timing 37 (FIG. 12) for capturing X-ray images 29 is determined in accordance with the respiratory waveform 26 (FIG. 6) and the rotational speed of the rotating gantry 12. In this way, appropriate control can be performed such that no X-ray images 29 are taken from the same direction in duplicate, thereby increasing imaging efficiency.

In the X-ray imaging device 18, the timing 37 (FIG. 12) for capturing X-ray images 29 is established in accordance with an acceleration term, a constant speed term, or a deceleration term of the rotation of the rotating gantry 12. In this way, imaging is performed during operation of the rotating gantry 12 at not only a constant speed, but also during acceleration and deceleration modes, resulting in a reduction in the total imaging time.

The control calculating device 16A stores information indicating the relation between a position of the affected area 40 (FIG. 13) in the patient 10 and the rotational angle θ. The timings 33, 34, 35, 36, and 37 (FIG. 10 to 12) of capture of the X-ray image 29 are determined in the X-ray imaging device 18 in accordance with the rotational angle θ. In this way, the X-ray image 29 can be taken from the appropriate direction in accordance with the position of the affected area 40.

The imaging conditions are established such that the X-ray images 29 taken by one first radiographic segment 14A and the X-ray images 29 taken by the other second radiographic segment 14B complement between their imaging angles. For example, the imaging conditions are established such that multiple X-ray images 29 categorized in the same fragment α of phase complement between their imaging angles. Such a scheme can reduce artifacts in the reconstructed images.

The imaging conditions to be established includes the rotation speed of the rotating gantry 12, which is based on the angle defined by the imaging directions of the first X-ray generating unit 13A and the second X-ray generating unit 13B and the cycle S (FIG. 6). In this way, the rotational speed of the rotating gantry 12 can be matched to the 29 X-ray images to be taken at an appropriate angle.

The imaging conditions are established such that the imaging angles at the time of each imaging in the multiple X-ray images 29 corresponding to the same fragment α of phase (specific fragment) are equally spaced. Such a mode can equalize shooting angles of the multiple X-ray images 29 corresponding to the same fragment α of phase and reduce the artifacts in the reconstructed images generated from these X-ray images 29.

Figure 10:
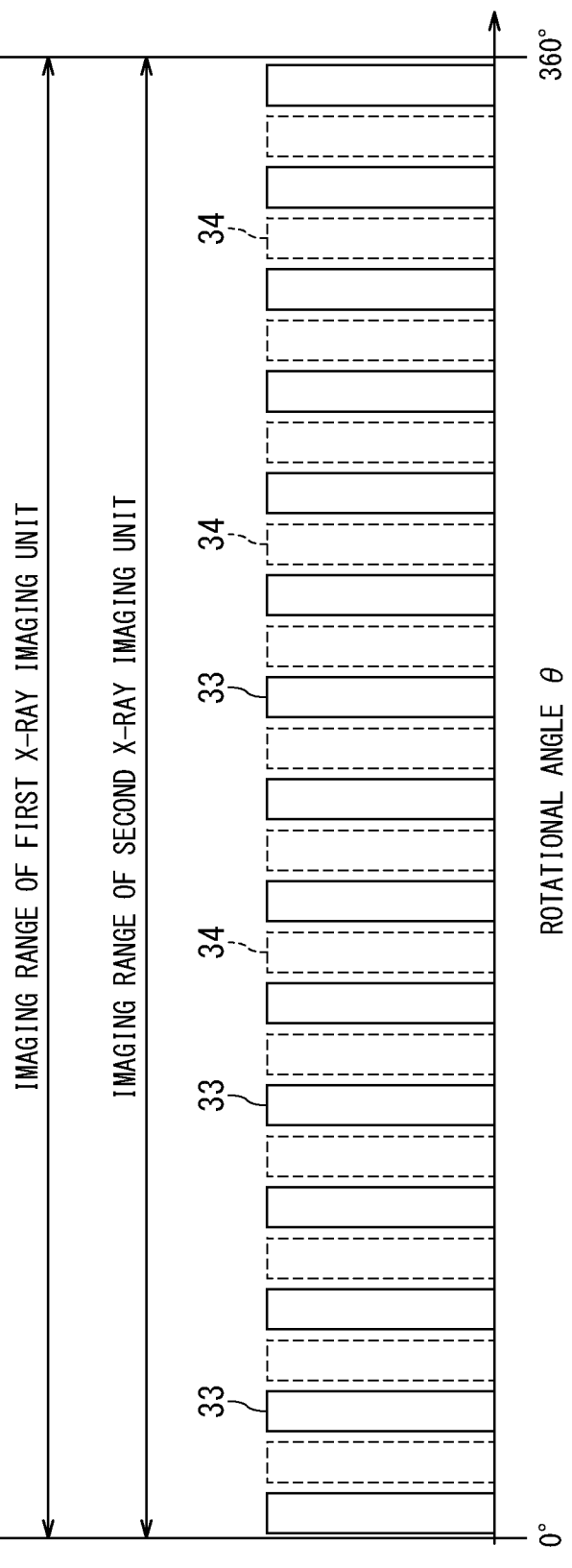
FIG. 10 is an illustrative view of a relation between the radiographic range of the radiographic unit and the rotational angle of the rotating gantry.
Figure 11:
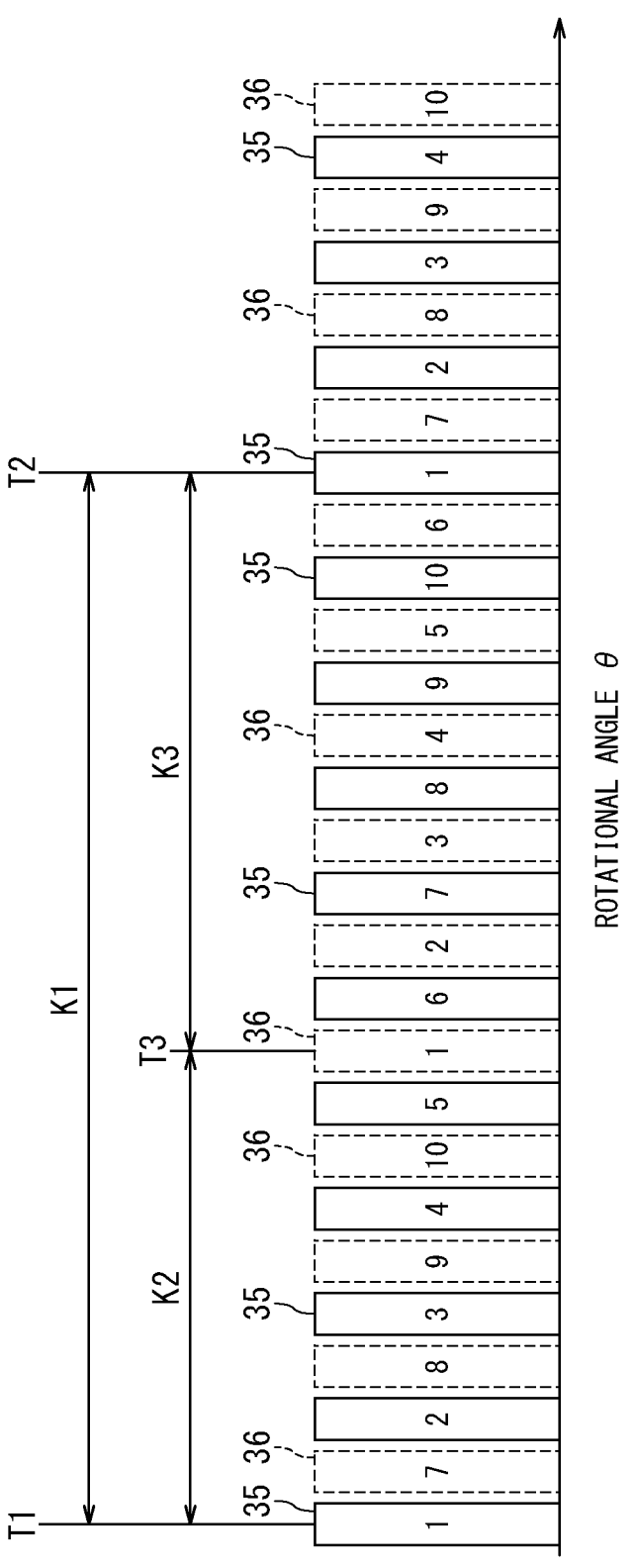
FIG. 11 is an illustrative view of a relation between the timing of the imaging of the radiographic unit and the rotational angle of the rotating gantry.
Figure 12:
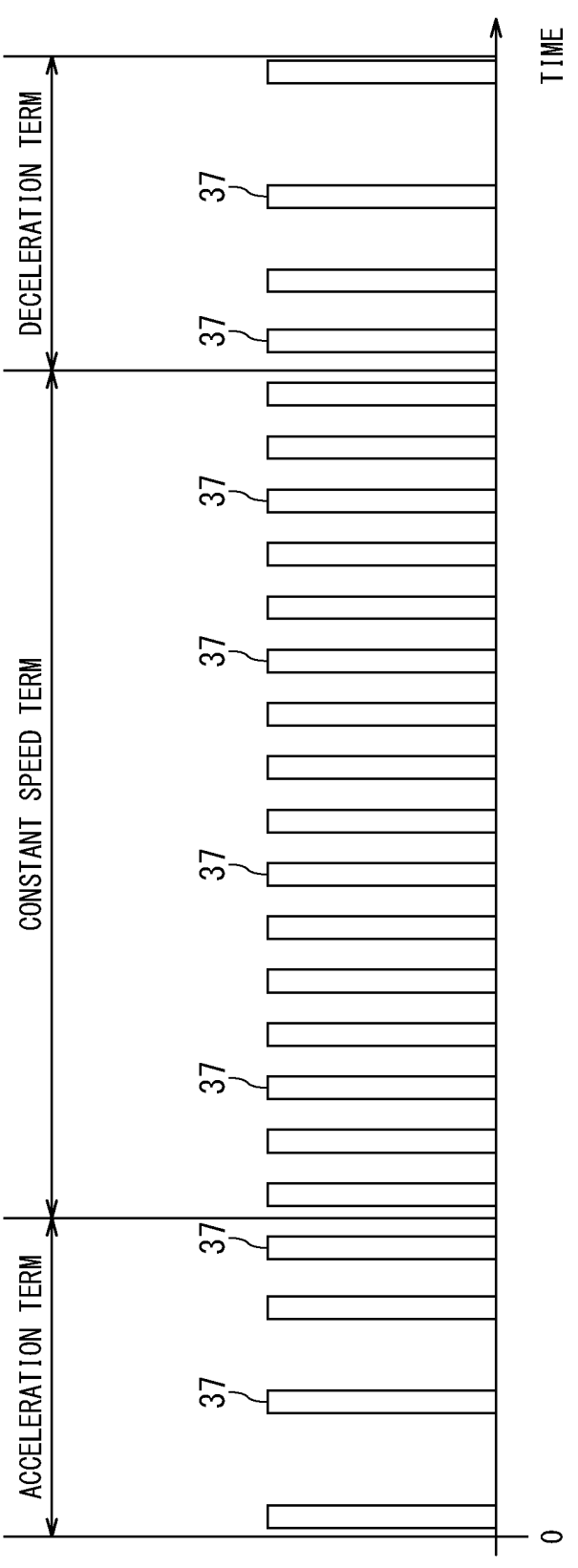
FIG. 12 is an illustrative view of a relation between the timing of the X-ray imaging and a rotational speed of the rotating gantry.

With reference to FIGS. 10 through 12, specific aspects of the establishments by the rotation setter 31 and the imaging setter 32 will now be described. Although, FIGS. 10 through 12 are described individually for the sake of understanding, these establishments can be used in combination with each other.

In FIG. 10, the horizontal axis represents the rotational angle θ (imaging angle) of the rotating gantry 12 when X-ray images 29 are taken and the vertical bars represent the timings 33 and 34 of shooting of the X-ray images 29. In FIG. 10, the timing 33 of shooting by the first radiographic segment 14A is depicted with solid bars, while the timing 34 of shooting by the second radiographic segment 14B is depicted with dotted bars. The imaging range by the first radiographic segment 14A and the imaging range of the second radiographic segment 14B overlap each other (are provided alternately).

The imaging setter 32 establishes the imaging conditions such that each timing 34 of shooting by the second radiographic segment 14B lies between two adjacent timings 33 of shooting by the first radiographic segment 14A. In this way, the X-ray images 29 taken by the first radiographic segment 14A and the X-ray images 29 taken by the second radiographic segment 14B complement the angles therebetween. Artifacts are reduced by generating a reconstructed image based on these X-ray image 29.

The rotational speed of the rotating gantry 12 during taking images at the timings 33 and 34 of shooting is determined on the basis of the angle defined by the imaging directions of the first radiographic segment 14A and the second radiographic segment 14B and the cycle S of the respiratory waveform 26 of the patient 10 (FIG. 6). The rotation setter 31 establishes the rotational speed of the rotating gantry 12 based on the determined imaging conditions. The timings 33 and 34 of shooting may also be determined based on the rotational angle θ of the rotating gantry 12. For example, the image may be taken when the rotational angle θ reaches the predetermined rotational angle θ, regardless of the rotational speed of the rotating gantry 12.

The imaging setter 32 should preferably establish the imaging conditions such that multiple X-ray images 29 categorized in the same fragment α of phase are taken at equal intervals or equal imaging angles.

In FIG. 11, the horizontal axis represents the rotational angle θ (imaging angle) of the rotating gantry 12 when the X-ray image 29 is taken, while the vertical bars represents the timings 35 and 36 of shooting of the X-ray images 29. In FIG. 11, the timing 35 of shooting by the first radiographic segment 14A is depicted with solid bars, while the timing 36 of shooting by the second radiographic segment 14B is depicted with dotted bars. For each of the timings 35 and 36 of shooting, a numeral from "1" to "10" is assigned to the corresponding fragment α of phase. The same numeral indicates that they resides in the same fragment α of phase.

Assuming that a predetermined timing T1 of the first radiographic segment 14A is categorized in the "1st" fragment α of phase and the next timing T2 of the first radiographic segment 14A is categorized in the same "1st" fragment α of phase. In this case, a shooting conditions are determined such that the timing T3 of the second radiographic segment 14B, which is categorized in the same "1st" fragment α of phase, is at approximately the middle position of the interval K1 between the timings T1 and T2. In other words, the imaging conditions are determined such that the imaging angles at the multiple X-ray images 29 corresponding to the same fragment α of phase (specific fragment) are at approximately the same interval.

The imaging conditions should preferably be determined such that the interval K2 from the timing T1 to the timing T3 is approximately identical to the interval K3 from the timing T3 to the timing T2 or the difference between them is minimized. At these timings T1, T2, and T3, X-ray images 29 categorized in the "1st" fragment α of phase are taken and reconstructed images are generated to reduce artifacts. The X-ray images 29 categorized in the other fragment α of phase are also taken in the same manner. Since moving images are generated with the reconstructed images obtained from these X-ray images 29, the moving images have reduced artifacts.

In FIG. 12, the horizontal axis indicates the time, while the bars on the vertical axis represent the shooting timing 37 of each X-ray image 29. FIG. 12 shows the shooting timing 37 of the rotating gantry 12 from a stopped state, start of rotation, rotation at a constant speed, deceleration, and then stop again. The shooting timing 37 corresponds to either one of the first radiographic segment 14A or the second radiographic segment 14B, or each of the first radiographic segment 14A and the second radiographic segment 14B. Only the shooting timing 37 by the radiographic unit 14 will be mentioned in the following description.

The imaging conditions on the shooting timings 37 by the radiographic unit 14 are determined such that imaging angles are equally spaced. For example, the interval between the shooting timings 37 gradually decreases during the acceleration term of the rotation of the rotating gantry 12. The interval between the shooting timings 37 is constant during the term of constant speed of the rotation of the rotating gantry 12. The interval between the shooting timings 37 gradually increases during the deceleration term of the rotation of the rotating gantry 12. Since the rotating gantry 12 is a large apparatus and its rotational speed is relatively slow, the acceleration and deceleration terms as well as the constant speed term can improve the efficiency of imaging. Furthermore, the shooting timings 33 and 34 (FIG. 10) can be secured over the entire circumference (360 degrees) of the rotating gantry 12. In other words, X-ray images 29 can be taken at angles equally spaced from each other over the entire circumference of the patient 10.

Figure 13:
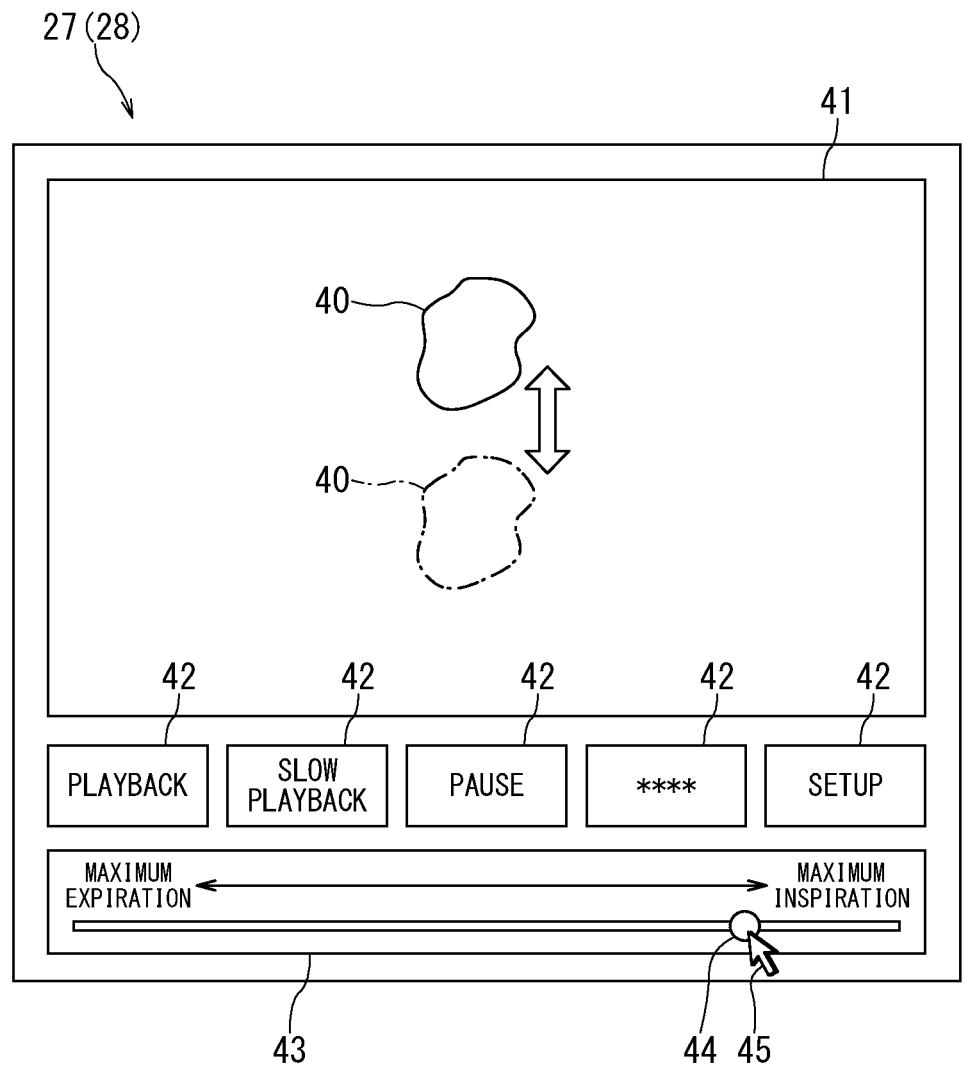
FIG. 13 is a schematic view of a screen illustrating a replay mode of a moving image on an affected area.

With reference to FIG. 13, the playback mode of the moving image consisting of the reconstructed images will now be described. The image generated at the control calculating device 16A is outputted to an external output unit 27 (FIG. 9). FIG. 13 illustrates an example screen appearing on the external output unit 27. The screen is also part of the user interface 28 (FIG. 9).

The screen is provided with a moving image display 41 that presents moving images of the affected areas 40. Upon playback of the moving image, the animation presents the affected area 40 moving in response to breathing. For example, the affected area 40 moving between maximum exhalation and maximum inhalation appears on the screen.

The screen also displays various selector keys 42 and an indicator 43. The indicator 43 extends from the left to the right, and a pointer 44 is also displayed that slides along the indicator 43.

The selector keys 42 includes "Playback," "Slow playback," and "Pause" keys for example. A setup key is also provided for calling a screen for performing a given "Setup". The user can operate the corresponding item by clicking on one of the selector keys 42 with a mouse cursor 45.

For example, when the user clicks on the "Playback" selector key 42, the moving image is played back. When the user clicks on the "Slow Playback" selector key 42, the moving image is played back in slow motion. When the user clicks on the "Pause" selector key 42, the playback of the moving image is temporarily stopped.

When the user clicks on the "Setup" selector key 42, the screen switches to a screen for performing predetermined settings. For example, the moving image can be played back in reverse, the screen can be enlarged or reduced, the contrast can be varied, or the moving image can be played back in frame-by-frame.

The indicator 43 also represent the state of respiratory cycle S of the displayed moving image. For example, the user can read the state of the moving image between the maximum expiration and maximum inspiration from the position of the pointer 44 on the indicator 43. For example, the pointer 44 on the indicator 43 repeatedly moves back and forth between the maximum exhalation and maximum inspiration, depending on the cycle S of respiration during playing back of the moving image.

When the user drags the pointer 44 on the indicator 43 left or right with the mouse cursor 45 while the moving image is paused, the moving image can be played back in frame by frame at a speed corresponding to the speed of the drag. The moving image can also be paused at any stage. In this way, the user can observe the condition of the affected area 40 at any point between the maximum exhalation and maximum inhalation.

As above, although the imaging control system 1 and the method of controlling imaging have been described on the basis of the first to third embodiments, the configuration applied in any one of the embodiments may be applied to other embodiments or the configurations in the respective embodiments may be applied in combination.

Although a mode in which each step is executed in series is illustrated in the flowchart of the above-described embodiments, the execution order of the respective steps is not necessarily fixed and the execution order of part of the steps may be changed. Additionally, some steps may be executed in parallel with another step.

The system in the above-described embodiments includes a storage device such as a Read Only Memory (ROM) and a Random Access Memory (RAM), an external storage device such as a Hard Disk Drive (HDD) and a Solid State Drive (SSD), a display device such as a display panel, an input device such as a mouse and a keyboard, a communication interface, and a control device which has a highly integrated processor such as a Central Processing Unit (CPU), a Graphics Processing Unit (GPU), a Field Programmable Gate Array (FPGA), and a special-purpose chip. The system can be achieved by hardware configuration with the use of the normal computer.

Note that the program executed in the system of the above-described embodiments is provided by being incorporated in a memory such as the ROM in advance. Additionally, or alternatively, the program may be provided by being stored as a file of installable or executable format in a non-transitory computer-readable storage medium such as a CD-ROM, a CD-R, a memory card, a DVD, and a flexible disk (FD).

In addition, the program executed in the system may be stored on a computer connected to a network such as the Internet and be provided by being downloaded via a network. Further, the system can also be configured by interconnecting and combining separate modules, which independently exhibit respective functions of the components, via a network or a dedicated line.

In the above-described embodiments, the control calculating device 16 slices at least one of the cycle S and amplitude L in the respiratory waveforms 26, 30 into multiple specific fragments. Any other aspect is also available. For example, the control calculating device 16 may slice both the cycle S and amplitude L in the respiratory waveforms 26, 30 into multiple specific fragments. The multiple X-ray images may then be categorized by both the fragment α of phase and the fragment β of amplitude.

In the above-described embodiments, although the numerals "1" to "10" are used as examples of the fragment identification information, any other form of fragment identification information may also be available. For example, fragment identification information may be the amount of movement of the affected area. Alternatively, fragment identification information may be the shooting time.

Although the X-ray imaging device 18 is equipped with two radiographic units 14 in the third embodiment, any number of radiographic units may be installed. For example, the X-ray imaging device 18 may be equipped with three or more radiographic units 14.

Although the foregoing embodiment illustrates a facility that provides heavy particle cancer therapy, the embodiment can be applied to other facilities. For example, the above-described embodiments may be applied to a facility that provides proton beam cancer therapy.

According to at least one of the embodiments described above, multiple X-ray images categorized by specific fragments are reconstructed based on the rotational angle of the rotating gantry during imaging to generate a three-dimensional reconstructed image. This allows the condition of the patient varying accompanied with respiratory motion to be accurately observed in computed tomography for radiation therapy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

REFERENCE SIGNS LIST

1 . . . imaging control system, 9 . . . sensor, 10 . . . patient, 11 . . . treatment table, 12 . . . rotating gantry, 13 . . . X-ray generator, 13A . . . first X-ray generating unit, 13B . . . second X-ray generating unit, 14 . . . radiographic unit, 14A . . . first radiographic segment, 14B . . . second radiographic segment, 15 . . . respiratory monitor, 16 (16A) . . . control calculating device, 17 . . . radioactive ray emitter, 18 . . . X-ray imaging device, 19A . . . first high-voltage generator, 19B . . . second high-voltage generator, 20 . . . gantry controller, 21 . . . prestage processor, 22 . . . respiratory waveform divider, 23 . . . image data sorter, 24 . . . 3D reconstructor, 25 . . . moving image generator, 26 . . . respiratory waveform, 27 . . . external output unit, 28 . . . user interface, 29 . . . X-ray image, 30 . . . respiratory waveform, 31 . . . rotation setter, 32 . . . imaging setter, 33, 34, 35, 36, 37 . . . timing of imaging, 40 . . . affected area, 41 . . . moving image display, 42 . . . selector key, 43 . . . indicator, 44 . . . pointer, 45 . . . mouse cursor, L . . . amplitude, Q . . . rotational axis, S . . . cycle, α . . . fragment of phase, β . . . fragment of amplitude, θ . . . rotational angle.

The invention claimed is:

1. An imaging control system comprising:
an X-ray imaging device to rotate together with a rotating gantry around a patient, to radiate X-rays to the patient for taking multiple two-dimensional X-ray images, and to output image data including the multiple two-dimensional X-ray images;
a respiratory monitor to watch respiratory motion of the patient and to output respiratory data indicating the respiratory motion;
a control calculating device to acquire the image data from the X-ray imaging device and to acquire the respiratory data from the respiratory monitor;
the control calculating device comprising:
a respiratory waveform divider to slice at least one of cycle and amplitude in a respiratory waveform of the respiratory motion included in the respiratory data into multiple specific fragments,
an image data sorter to acquire a rotational angle indicating a rotational position of the rotating gantry from a gantry controller for controlling a rotation of the rotating gantry, and to sort the multiple two-dimensional X-ray images contained in the image data by each of the multiple specific fragments into the multiple two-dimensional X-ray images, and a three-dimensional reconstructor to reconstruct the multiple two-dimensional X-ray images categorized by each of the multiple specific fragments based on the rotational angle of the rotating gantry at shooting to generate multiple three-dimensional reconstructed images, wherein the control calculating device is configured to determine whether the image data is appropriate for generating the multiple three-dimensional reconstructed images, and to discard at least a portion of the image data that is determined to be inappropriate; and the control calculating device determines that, for the multiple two-dimensional X-ray images acquired during one rotation of the rotating gantry and categorized in each predetermined fragment of amplitude in the respiratory waveform, the image data is inappropriate for generating the multiple three-dimensional reconstructed images in a case of uneven numbers of the multiple two-dimensional X-ray images among each predetermined fragment of amplitude in the respiratory waveform, and discards all the image data at that time without generation of the multiple three-dimensional reconstructed images.

2. The imaging control system according to claim 1, wherein the control calculating device further comprises a moving image generator to generate a moving image from the multiple three-dimensional reconstructed images along a time axis of the respiratory waveform and to output the moving image.

3. The imaging control system according to claim 1, wherein the control calculating device further comprises a moving image generator to generate a moving image capable of being played back from maximum inspiration and maximum expiration from the multiple three-dimensional reconstructed images and to output the moving image.

4. The imaging control system according to claim 1, wherein the control calculating device preliminarily stores information on a divisional region and a number of divisions for slicing the amplitude into the multiple specific fragments.

5. The imaging control system according to claim 1, wherein the X-ray imaging device is configured to perform shooting prior to irradiation of the patient with therapeutic radiation, and the control calculating device is configured to generate the multiple three-dimensional reconstructed images for use in matching with a standard image for treatment regimen acquired in advance.

6. The imaging control system according to claim 1, wherein the X-ray imaging device is configured to establish a timing of shooting the multiple two-dimensional X-ray images in accordance with the respiratory waveform and a rotational speed of the rotating gantry.

7. The imaging control system according to claim 1, wherein the X-ray imaging device is configured to establish a timing of shooting the multiple two-dimensional X-ray images in accordance with each of an acceleration term, a constant speed term, and a deceleration term of the rotation of the rotating gantry.

8. The imaging control system according to claim 1, wherein the control calculating device is configured to store information indicating a relation between a position of an affected area in the patient and the rotational angle, and the X-ray imaging device is configured to establish a timing of shooting of the multiple two-dimensional X-ray images in accordance with the rotational angle.

9. The imaging control system according to claim 1, wherein the control calculating device is configured to correlate fragment-identifying information capable of identifying the multiple specific fragments with the rotational angle at the shooting for managing the multiple two-dimensional X-ray images.

10. The imaging control system according to claim 1, wherein the X-ray imaging device comprises at least two radiographic units for taking the multiple two-dimensional X-ray images at multiple shooting angles accompanied by the rotation of the rotating gantry; and the X-ray imaging device is configured to establish a shooting condition such that an X-ray image taken by a first radiographic unit of the at least two radiographic units and another X-ray image taken by a second radiographic unit of the at least two radiographic units complement between their imaging angles.

11. The imaging control system according to claim 10, wherein an establishment of the shooting condition includes the establishment of a rotational speed of the rotating gantry; and the rotational speed of the rotating gantry is determined based on an angle defined by shooting directions of the first radiographic unit and the second radiographic unit.

12. The imaging control system according to claim 10, wherein the shooting condition is established such that the multiple shooting angles at a times of shooting in the multiple two-dimensional X-ray images corresponding to one of the multiple specific fragments are equally spaced.

13. An imaging control method comprising steps of:

acquiring a rotational angle indicating a rotational position of a rotating gantry rotating around a patient from a gantry controller that controls the rotating gantry;

acquiring image data from an X-ray imaging device that outputs the image data including multiple two-dimensional X-ray images taken by the X-ray imaging device rotating with the rotating gantry and radiating X-rays to the patient;

acquiring respiration data from a respiration monitor that watches respiratory motion of the patient and to output the respiration data indicating the respiratory motion;

slicing at least one of cycle and amplitude in a respiratory waveform of the respiratory motion included in the respiration data into multiple specific fragments;

categorizing the multiple two-dimensional X-ray images contained in the image data based on each of the multiple specific fragments;

reconstructing the multiple two-dimensional X-ray images categorized every specific fragment based on the rotational angle of the rotating gantry at a time of shooting to produce a three-dimensional reconstructed image, wherein, in the reconstructing of the multiple two-dimensional X-ray images, it is determined whether the image data is appropriate for generating the three-dimensional reconstructed image, and at least a portion of the image data that is determined to be inappropriate is discarded; and it is determined that, for the multiple two-dimensional X-ray images acquired during one rotation of the rotating gantry and categorized in each predetermined fragment of amplitude in the respiratory waveform, the image data is inappropriate for generating multiple three-dimensional reconstructed images in a case of uneven numbers of X-ray images among predetermined fragments of amplitude, and all image data acquired at that time is discarded without generation of the multiple three-dimensional reconstructed images.

14. The imaging control system according to claim 1, wherein the control calculating device determines that if the number of the multiple two-dimensional X-ray images categorized into a certain fragment of amplitude among predetermined fragments of amplitude is insufficient for generating the multiple three-dimensional reconstructed, the image data is inappropriate for generating the multiple three-dimensional reconstructed, and discards the multiple two-dimensional X-ray images categorized into the certain fragment of amplitude.

* * * * *